US007709634B2

(12) United States Patent
Kothakonda et al.

(10) Patent No.: US 7,709,634 B2
(45) Date of Patent: May 4, 2010

(54) AMORPHOUS FORM OF RIFAXIMIN AND PROCESSES FOR ITS PREPARATION

(75) Inventors: Kiran Kumar Kothakonda, Brantford (CA); Daqing Che, Brantford (CA)

(73) Assignee: Apotex PharmAchem Inc., Brantford (CA)

( * ) Notice: Subject to any disclaimer, the term of this patent is extended or adjusted under 35 U.S.C. 154(b) by 0 days.

(21) Appl. No.: 11/902,211

(22) Filed: Sep. 20, 2007

(65) Prior Publication Data
US 2009/0082558 A1 Mar. 26, 2009

(51) Int. Cl.
*C07D 498/22* (2006.01)
(52) U.S. Cl. ..................................... 540/456
(58) Field of Classification Search ........... 540/456
See application file for complete search history.

(56) References Cited

U.S. PATENT DOCUMENTS

| | | | |
|---|---|---|---|
| 4,341,785 | A | 7/1982 | Marchi et al. |
| 4,557,866 | A | 12/1985 | Cannata |
| 6,869,974 | B1 | 3/2005 | Del Soldato |
| 6,987,120 | B1 | 1/2006 | Del Soldato |
| 7,045,620 | B2 | 5/2006 | Viscomi et al. |
| 7,186,753 | B1 | 3/2007 | Del Soldato |
| 2005/0272754 | A1 | 12/2005 | Viscomi |
| 2006/0110447 | A1 | 5/2006 | Chiarelli |
| 2008/0132530 | A1 | 6/2008 | Viscomi |

FOREIGN PATENT DOCUMENTS

| | | |
|---|---|---|
| CA | 1215976 | 12/1986 |
| CA | 1218650 | 3/1987 |
| EP | 161534 | 9/1989 |
| EP | 0675126 | 10/1995 |
| EP | 1698630 | 9/2006 |
| GB | 2079270 | 1/1982 |
| JP | 1996034730 | 2/1996 |
| WO | 2006094662 | 9/2006 |
| WO | 2008029208 | 3/2008 |
| WO | WO2008/035109 | 3/2008 |
| WO | WO2008/155728 | 12/2008 |

OTHER PUBLICATIONS

Konno, Tsutomu, "Physical and chemical changes of medicinals in mixtures with adsorbents in the solid state . . . ", Chem. Pharm. Bull., 38(7), 2003-7, (1990).
Cellai et al. Structure-activity relationships in 4-deoxypyrido(1',2'-1,2)imidazo(5,4-c)rifamycin SV derivatives. Mediterr. Congr. Chemother., Proc., 3rd, 1982), 53-4.
Cellai, L. A study of structure-activity . . . Molecular Pharmacology (1985), 27(1), 103-8.
Cellai, L. et al. Synthesis of tritium-labeled rifamycin L 105. Journal of Labelled Compounds and Radiopharmaceuticals (1983), 20(11), 1287-96.

(Continued)

*Primary Examiner*—Bruck Kifle

(57) ABSTRACT

A stable amorphous form of rifaximin is disclosed. This form is chemically and polymorphically stable on storage and can be prepared by dissolving rifaximin in a solvent to form a solution, which is precipitated by adding an anti-solvent and isolating of the precipitated amorphous rifaximin as an end product.

16 Claims, 2 Drawing Sheets

OTHER PUBLICATIONS

Corti, P. et al. Application of derivative resolution of UV spectra to the quality control of rifaximine and its possible impurities. Pharmaceutica Acta Helvetiae (1992), 67(3), 76-9.

Corti, P. et al. Thin-layer chromatography in the quantitative analysis of drugs. Determination of rifaximin and its oxidation products. . Analusis (1991), 19(8), 257-61.

Corti, P. et al. Application of near-infrared reflectance spectroscopy (NIRS) to several antibiotic compounds. Process Control and Quality (1992), 2(2), 131-42.

Fu et al. (2005) determination for rifaximin content in its capsules. Guangdong Yaoxueyuan Xuebao 21(3), 272-273.

Lu, H. et al. Separation and Determination of Rifaximin and Quinone-Rifaximin by HPLC. Yaowu Fenxi Zazhi (2004), 24(3), 333-335.

Marchi, E. et al. L_105 a new semisynthetic derivative of rifamycin. Suppl. Mediterr. Congr. Chemother., Proc., 3rd, 1982), 48-50.

Meng, XJ. NMR and MS of Rifaximin. Guangpu Shiyanshi (2003), 20(1), 31-34.

Wang, J. et al. RP-HPLC determination of rifaximin.Zhongguo Xinyao Zazhi (2003), 12(11), 932-934.

Zhang, X. et al. Sensitive quantification of rifaximin in human plasma by liquid chromatography-tandem mass spectrometry. J.of Chroma. Ana. Tech. in the Biomed. and Life Sci. (2007), 850(1-2), 348-355.

Zhang, Z. Determination of rifaximin and its related substances by RP-HPLC. Huaxi Yaoxue Zazhi (2003), 18(4), 281-283.

Brufani, M. et al. The synthesis of 4-deoxypyrido[1',2'-1,2]imidazo[5,4-c]rifamycin SV derivatives. Journal of Antibiotics (1984), 37(12), 1611-22.

AMORPHOUS FORM OF RIFAXIMIN AND PROCESSES FOR ITS PREPARATION

FIELD OF THE INVENTION

This invention discloses a stable and novel amorphous form of rifaximin prepared by the judicious combination of dissolution solvent and anti-solvent.

BACKGROUND OF THE INVENTION

Rifaximin (1) {(2S,16Z,18E,20S,21S,22R,23R,24R,25S, 26S,27S,28E)-5,6,21,23,25-pentahydroxy-27-methoxy-2,4, 11,16,20,22,24,26-octamethyl-2,7-(epoxypentadeca-[1,11, 13]trienimino)benzofuro[4,5-e]pyrido[1,2-α]-benzimidazole-1,15(2H)-dione,25-acetate} is a semisynthetic rifamycin-based non-systemic antibiotic marketed in the US as Xifaxan® by Salix Pharmaceuticals.

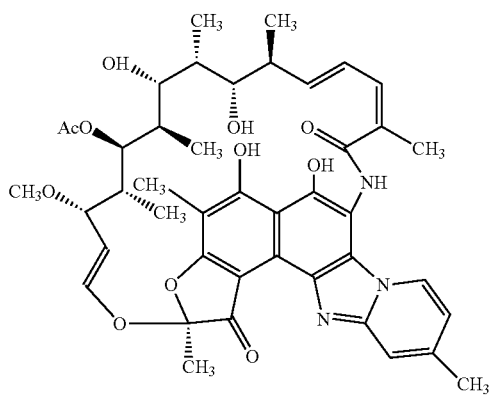

1, Rifaximin (Xifaxan®)

It is useful for the treatment of travelers diarrhea in adults and in children 12-years of age and older caused by *E. coli* bacteria. Rifaximin has also been evaluated for the treatment of irritable bowel syndrome, diverticular disease, hepatic encephalopathy, pyogenic skin infections, and as an antibacterial prophylactic prior to colon surgery. Medical News Today has recently published an article detailing a study conducted by physicians at New York-Presbyterian Hospital/ Weill Cornell Medical Center using rifaximin for the treatment of patients who suffer from severe Crohn's disease and who have not responded to all other available medications.

Structurally rifaximin is a pyrido-imidazo derivative of rifamycin SV (4-deoxy-4'-methylpyrido[1',2':1,2]imidazo[5, 4-c]rifamycin SV). Unlike other rifamycin SV derivatives, rifaximin exerts broad spectrum activity and has a specific mode of action which results in low gastrointestinal absorption.

GB 2,079,270 disclose imidazo-rifamycin derivatives having antibacterial activity, prepared from 3-halorifamycin S. U.S. Pat. No. 4,341,785 and EP 0,161,534 (Alpha Farmaceutici SpA) describe the processes for preparing pyrido-imidazo rifamycin starting from rifamycin O. The above patents detail a generic method for the purification of rifaximin in suitable solvent systems such as methylene chloride, chloroform, methanol, ethanol, isopropanol. Water is generally used as an anti-solvent. The polymorphic form of the rifaximin obtained by these methods was not disclosed.

Recently, three polymorphic forms of rifaximin were described in U.S. Pat. No. 7,045,620 (Alfa Wassermann SpA) and designated as α, β, γ. The point of differentiation between these forms is their respective water contents and powder X-ray diffraction (PXRD) diffractogram. These forms are inter-convertible and, therefore, obtaining a specific polymorphic form is dependent on the drying conditions. The γ-form of U.S. Pat. No. 7,045,620 is described as being poorly crystalline with a high content of amorphous component. It is characterized as having a water content between 1.0% and 2.0% and having a PXRD diffractogram containing a few significant peaks at 5.0, 7.1 and 8.4 (two-theta). In particular, this form is prepared by dissolution of in ethanol followed by the addition of water. Also noteworthy is that this form is prone to conversion to other polymorphic forms on exposure to, for instance, due to the change in its water content level. This is a disadvantage since it is highly desirable to have an active pharmaceutical ingredient which is polymorphically stable and suitable for pharmaceutical applications (see Konne, T., Chem. Pharma. Bull., 38, p. 2003, (1990)).

EP 1,698,630 (Alfa Wassermann SpA) teaches two new polymorphic forms (δ, ε). These forms are also obtained from the same process method described above and their specific crystal structures are again dependent of water content and there is a degree of overlap with the other purported forms.

Therefore, it is an object of the present invention to provide a polymorphically pure and stable form of rifaximin, prepared by utilizing industrially acceptable procedures, which overcomes the deficiencies of the prior art.

Further and other objects of the invention will become apparent to those skilled in the art when considering the following summary of the invention and the more detailed description of the embodiments of the invention described herein.

SUMMARY OF THE INVENTION

According to one aspect of the present invention there is disclosed a stable amorphous form of rifaximin. Preferably, the stable amorphous form of rifaximin is characterized by having X-ray powder diffraction pattern peaks, as reported in FIG. 1, expressed in 2θ values at about 7.2°; 15.0° and Differential Scanning Calorimetry (DSC) thermogram as shown in FIG. 2.

According to another aspect of the invention there is provided a process for the preparation of stable amorphous form of rifaximin which comprises:
  a) dissolving crude rifaximin in a solvent to form a solution,
  b) precipitating said solution by adding an anti-solvent, or optionally precipitating by adding the solution of step (a) to an anti-solvent, and
  c) isolating the precipitated rifaximin by filtration and drying at ambient temperature.

The present invention uses industrially acceptable class-3 solvents, as listed in the ICH Q3C (R3) guidelines, throughout the process. In contrast to the previous methods, the method of the instant invention does not use water which is a disadvantage for a hygroscopic material.

In the preferred embodiments of this invention, the crude rifaximin is dissolved in solvents selected from $C_3$ to $C_6$ alkyl esters, for instance methyl acetate, ethyl acetate, isopropyl acetate; $C_1$-$C_6$ lower alkanols, for instance ethanol, isopropanol, 2-butanol; and $C_3$-$C_6$ alkyl ketones, for instance, acetone, methyl iso-butyl ketone (MIBK).

The temperature of this solution could be between 0° C. to reflux, preferably 10 to 55° C. and most preferably 15-45° C. The volumes used can be 1 to 25 volumes, preferably 1.5 to 12 volumes and most preferably 2 to 6 volumes. Optionally, the solution could be clarified by, for instance, filtration through a Buchner funnel or cartridge filter.

The anti-solvent is added to rifaximin containing solution in order to precipitate the amorphous rifaximin. Suitable anti-solvents include $C_5$ to $C_{10}$ hydrocarbons, such as heptanes; $C_4$ to $C_8$ alkyl ethers, such as methyl tert-butyl ether; or mixtures thereof. The most preferable anti-solvents are heptanes and methyl tert-butyl ether (MTBE), or mixtures thereof. The volume of antisolvent is between 1 to 36 volumes, preferably 2 to 20 volumes and most preferably 3 to 10 volumes.

In another embodiment of the present invention, the rifaximin solution is added to an anti-solvent. This type of addition is known in the art as reverse addition.

The addition and precipitation temperature is from about −20° C. to about 55° C., preferably about 0° C. to about 45° C. and most preferably about 10 to about 35° C.

Significantly, these processes are robust and independent of any critical parameters and the form produced is completely amorphous. Surprisingly, this form is chemically and polymorphically stable on storage and is relatively unaffected by external parameters such as ambient humidity. For instance, exposure of the amorphous form of the present invention to ambient humidity for a period of 10 days did not change the polymorphic form as indicated by PXRD spectroscopy. High yield of amorphous form of rifaximin is isolated by the processes of the present invention and it has high chemical purity and retains acceptable amounts of residual solvents.

The following non-limiting examples further illustrate the manner of carrying out the inventive process described herein.

EXAMPLE 1

Figure 1:
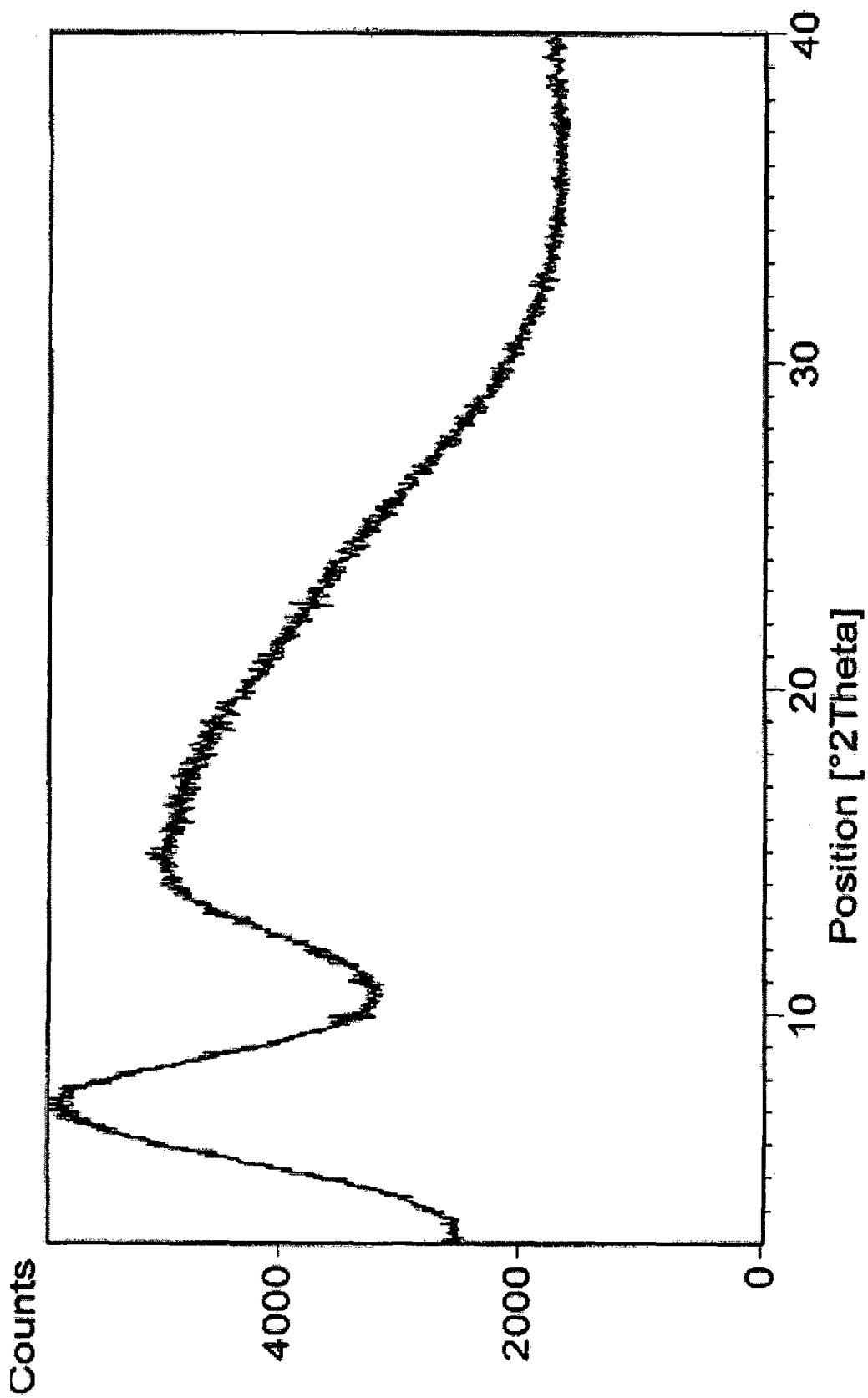
FIG. 1 illustrates the powder X-ray diffraction pattern of amorphous pattern of amorphous form of rifaximin.
Figure 2:
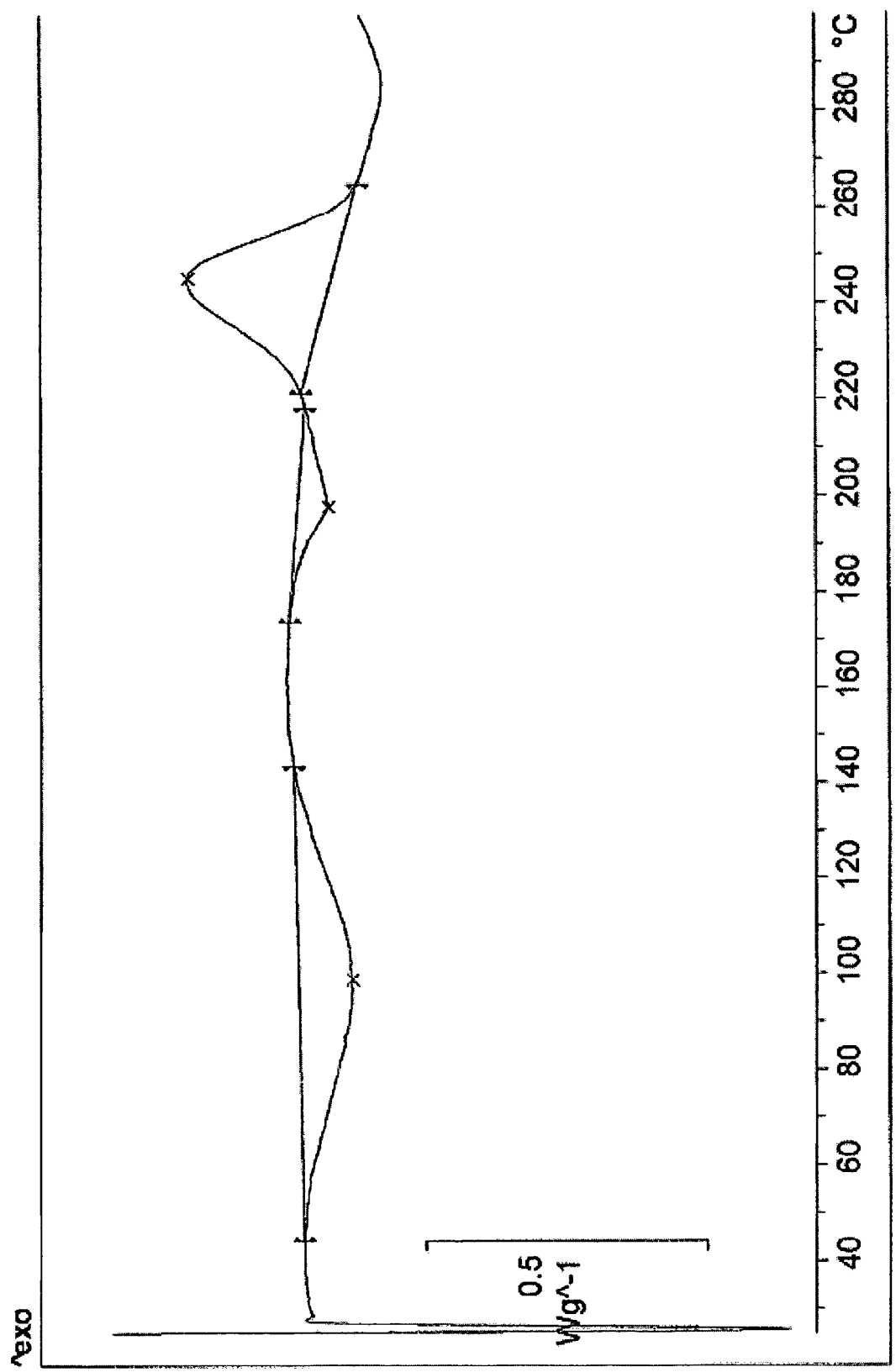
FIG. 2 illustrates the differential scanning calorimetry thermogram of amorphous form of rifaximin.

Crude rifaximin (50 g) was dissolved in ethyl acetate (150 mL) in a three necked flask under nitrogen and filtered off to remove insoluble material. Heptanes (150 mL) were added slowly at ambient temperature. After complete precipitation, the precipitated product was isolated by filtration and dried at ambient temperature in a vacuum oven to obtain 41 g (82%) of pure amorphous rifaximin. The PXRD diffractogram and DSC thermogram are essentially the same as depicted in FIGS. 1 and 2, respectively.

EXAMPLE 2

Rifaximin (25 g) was charged to a three necked flask along with 4 volumes of ethyl acetate under nitrogen and stirred to dissolve. This solution was clarified by filtration through a Buchner funnel and then added to 6 volumes of heptanes at room temperature. After complete precipitation, the product was isolated by Buchner filtration and dried in a vacuum oven at ambient temperature to provide 23 g (92%) of pure amorphous rifaximin. The PXRD diffractogram and DSC thermogram are essentially the same as depicted in FIGS. 1 and 2, respectively.

EXAMPLE 3

Rifaximin (10 g) was dissolved in acetone (35 mL) in a three necked flask under nitrogen. One volume was removed by distillation, and the hot solution was allowed to cool and filtered to remove insoluble material. This solution was added to heptanes (10 vol). After complete precipitation, the precipitated material was isolated by filtration and dried at ambient temperature in a vacuum oven to provide 5 g of amorphous rifaximin. The PXRD diffractogram and DSC thermogram are essentially the same as depicted in FIGS. 1 and 2, respectively.

EXAMPLE 4

Rifaximin (5 g) was charged into a three necked flask along with 2-butanol (50 mL) under nitrogen and the mixture was stirred to dissolve. The solution was added to heptanes (16 vol). After complete precipitation, the precipitated amorphous rifaximin was isolated by filtration and dried at ambient temperature in a vacuum oven to provide 4.1 g (82%) of amorphous rifaximin. The PXRD diffractogram and DSC thermogram are essentially the same as depicted in FIGS. 1 and 2, respectively.

EXAMPLE 5

Rifaximin (10 g) was dissolved in 5 volumes of methyl iso-butyl ketone in a three necked flask under nitrogen. The solution was clarified by Buchner filtration and the solution was added to 5 volumes heptanes. After complete precipitation, the product was isolated by filtration and dried at ambient temperature in a vacuum oven to provide 9 g (90%) amorphous rifaximin. The PXRD diffractogram and DSC thermogram are essentially the same as depicted in FIGS. 1 and 2, respectively.

EXAMPLE 6

Crude rifaximin (5 g) was charged to a three necked flask, followed by 4 volumes of ethyl acetate under nitrogen and the mixture was stirred to dissolve. The solution was clarified by filtration into a flask and this saturated solution was added to methyl tert-butyl ether (16 vol). After complete precipitation, it was filtered and the isolated product was dried in a vacuum oven at ambient temperature to obtain 2.4 g of amorphous rifaximin. The PXRD diffractogram and DSC thermogram are essentially the same as depicted in FIGS. 1 and 2, respectively.

While the foregoing provides a detailed description of the preferred embodiment and examples of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The invention claimed is:

1. A compound, which is an amorphous form of rifaximin having substantially the same X-ray powder diffraction pattern as shown in FIG. 1.

2. A process for the preparation of an amorphous form of rifaximin, said process comprising:
  i. dissolving rifaximin in a solvent selected from the group consisting of $C_3$ to $C_6$ alkyl esters, $C_2$ to $C_4$ alcohols, $C_3$ to $C_7$ alkyl ketones, and mixtures thereof to form a solution;
  ii. optionally distilling said solution;
  iii. optionally filtering said solution;
  iv. precipitating said solution by adding an anti-solvent selected from the group consisting of $C_5$ to $C_{10}$ hydrocarbons, $C_4$ to $C_8$ alkyl ethers, and mixtures thereof, or optionally precipitating by adding the solution to the anti-solvent, v. isolating of said precipitated amorphous rifaximin; and
vi. optionally drying the amorphous rifaximin.

3. The process of claim 2 wherein said solvent is selected from methyl acetate, ethyl acetate, isopropyl acetate, isobutyl acetate, ethanol, isopropanol, 2-butanol, acetone, methyl isobutyl ketone or mixtures thereof.

4. The process of claims 2 or 3 wherein the amount of said solvent is 1 to 25 volumes.

5. The process of claims 2 or 3 wherein the amount of solvent is 1.5 to 12 volumes.

6. The process of claims 2 or 3 wherein the amount of solvent is 2 to 6 volumes.

7. The process of claim 2 wherein the anti-solvent is selected from heptanes, methyl tert-butyl ether, or mixtures thereof.

8. The process of claims 2 or 7 wherein the amount of anti-solvent is 1 to 36 volumes.

9. The process of claims 2 or 7 wherein the amount of anti-solvent is 2 to 20 volumes.

10. The process of claims 2 or 7 wherein the amount of anti-solvent is 3 to 10 volumes.

11. The process of claim 2 wherein step (i) solution is maintained at a temperature of between 0° C. to reflux temperature.

12. The process of claim 2 wherein step (i) solution is maintained at a temperature of between 10° to 55° C.

13. The process of claim 2 step (i) solution is maintained at a temperature of between 15° to 45° C.

14. The process of claim 2 wherein the addition and precipitation temperature is −20° to 55° C.

15. The process of claim 2 wherein the addition and precipitation temperature is 0° to 45° C.

16. The process of claim 2 wherein the addition and precipitation temperature is 10° to 35° C.

* * * * *